(12) United States Patent
Harbindu et al.

(10) Patent No.: US 10,519,116 B2
(45) Date of Patent: Dec. 31, 2019

(54) WATER-SOLUBLE PYRAZOLE DERIVATIVES AS CORROSION INHIBITORS

(71) Applicant: Ecolab USA Inc., St. Paul, MN (US)

(72) Inventors: Anand Harbindu, Shahjahanpur (IN); Jothibasu Seetharaman, Cuddalore (IN); Jeffery M. Atkins, Aurora, IL (US); Deepak Rane, Mumbai (IN); Vaideeswaran Sivaswamy, Pune (IN)

(73) Assignee: Ecolab USA Inc., St. Paul, MN (US)

( * ) Notice: Subject to any disclaimer, the term of this patent is extended or adjusted under 35 U.S.C. 154(b) by 339 days.

(21) Appl. No.: 15/166,536

(22) Filed: May 27, 2016

(65) Prior Publication Data

US 2016/0347716 A1    Dec. 1, 2016

Related U.S. Application Data

(60) Provisional application No. 62/167,710, filed on May 28, 2015.

(51) Int. Cl.
 *C23F 11/00* (2006.01)
 *C23F 11/04* (2006.01)
 (Continued)

(52) U.S. Cl.
 CPC ......... *C07D 231/12* (2013.01); *C07D 231/16* (2013.01); *C07D 231/56* (2013.01); *C07D 249/18* (2013.01); *C23F 11/149* (2013.01)

(58) Field of Classification Search
 CPC ....... C23F 11/182; C23F 11/00; C23F 11/149; C02F 1/00
 (Continued)

(56) References Cited

U.S. PATENT DOCUMENTS 3,408,307 A   10/1968   Troscinski et al.
3,615,616 A   10/1971   Wilrijk et al.
(Continued)

FOREIGN PATENT DOCUMENTS

CN   103436888 A   12/2013
EP   0215670 A2   3/1987
(Continued)

OTHER PUBLICATIONS

Attayibat, A. et al., "Quantum Chemical Studies on N-Donors Based-Pyrazole Compounds as Corrosion Inhibitors for Steel in Acidic Media," Asian Journal of Chemistry, 2009, vol. 21, No. 1; pp. 105-112.*

(Continued)

*Primary Examiner* — Monzer R Chorbaji
(74) *Attorney, Agent, or Firm* — Leydig Voit and Mayer, Ltd.

(57) ABSTRACT

Disclosed are nitrogen-containing heterocyclic compounds of relatively low aquatic toxicity and methods of using the heterocyclic compounds as corrosion inhibitors. The present method is used to inhibit corrosion of a metal surface in contact with an aqueous system using pyrazole derivatives, and provides enhanced protection against corrosion of metals in aqueous systems. The method comprises the use of corrosion inhibitors that are generally resistant to halogen attack and provide good corrosion resistance in the presence of oxidizing halogen-based biocides. Formulations comprising pyrazole derivatives are also disclosed.

15 Claims, 5 Drawing Sheets

(51) Int. Cl.
  *C09K 3/00* (2006.01)
  *C07D 231/12* (2006.01)
  *C07D 249/18* (2006.01)
  *C07D 231/16* (2006.01)
  *C07D 231/56* (2006.01)
  *C23F 11/14* (2006.01)

(58) Field of Classification Search
  USPC .................. 422/7, 12–14, 16; 427/420, 427; 252/387
  See application file for complete search history.

(56) References Cited

U.S. PATENT DOCUMENTS

| | | | |
|---|---|---|---|
| 4,134,959 | A | 1/1979 | Menke et al. |
| 4,142,029 | A | 2/1979 | Illy |
| 4,306,986 | A * | 12/1981 | Schiessl ............... C07D 231/12 252/390 |
| 4,395,294 | A | 7/1983 | Hobbins et al. |
| 4,758,312 | A | 7/1988 | Hunt et al. |
| 5,082,611 | A | 1/1992 | Adams et al. |
| 5,128,065 | A | 7/1992 | Hollander |
| 5,156,769 | A | 10/1992 | Cha et al. |
| 5,455,220 | A | 10/1995 | Dedolph |
| 5,468,410 | A | 11/1995 | Angevaare et al. |
| 5,744,424 | A | 4/1998 | Dedolph |
| 5,746,947 | A | 5/1998 | Vanderpool et al. |
| 5,874,026 | A | 2/1999 | Pilsits, Jr. et al. |
| 6,103,144 | A | 8/2000 | Cheng |
| 6,203,719 | B1 | 3/2001 | Turcotte et al. |
| 6,379,587 | B1 | 4/2002 | Chen |
| 6,572,789 | B1 | 6/2003 | Yang et al. |
| 6,585,933 | B1 | 7/2003 | Ehrhardt et al. |
| 6,646,082 | B2 * | 11/2003 | Ghosh ..................... C08F 22/40 526/258 |
| 7,393,395 | B2 | 7/2008 | Aiba et al. |
| 7,968,507 | B2 | 6/2011 | Lee et al. |
| 7,972,655 | B2 | 7/2011 | Abys et al. |
| 8,361,237 | B2 | 1/2013 | Wu et al. |
| 9,074,170 | B2 | 7/2015 | Barnes et al. |
| 2003/0063998 | A1 | 4/2003 | Ghosh et al. |
| 2003/0065116 | A1 | 4/2003 | Ghosh et al. |
| 2010/0123100 | A1 | 5/2010 | Gill et al. |
| 2010/0152086 | A1 | 6/2010 | Wu et al. |
| 2010/0163469 | A1 | 7/2010 | Wan et al. |
| 2010/0197136 | A1 | 8/2010 | Shimada et al. |
| 2011/0318929 | A1 | 12/2011 | Mishima et al. |
| 2012/0108489 | A1 | 5/2012 | Miralles |
| 2012/0283163 | A1 | 11/2012 | Barnes et al. |
| 2013/0295292 | A1 | 11/2013 | Bukeikhanova et al. |
| 2014/0044593 | A1 | 2/2014 | Garner |
| 2015/0152329 | A1 | 6/2015 | Seetharaman et al. |
| 2016/0032221 | A1 | 2/2016 | Barnes et al. |

FOREIGN PATENT DOCUMENTS

| | | |
|---|---|---|
| EP | 0226016 A1 | 6/1987 |
| EP | 0634460 A2 | 1/1995 |
| EP | 1288232 A2 | 3/2003 |
| EP | 2199379 A1 | 6/2010 |
| JP | 2002-323741 A | 11/2002 |
| JP | 2006-079093 A | 3/2006 |
| KR | 10-2013-0011943 A | 1/2013 |
| KR | 20140020432 A | 2/2014 |
| WO | WO 90/10732 A1 | 9/1990 |
| WO | WO 96/20295 A1 | 7/1996 |
| WO | WO 96/29449 A1 | 9/1996 |
| WO | WO 97/39610 A1 | 10/1997 |
| WO | WO 99/33824 A1 | 7/1999 |
| WO | WO 02/00965 A1 | 1/2002 |
| WO | WO 02/10326 A1 | 2/2002 |
| WO | WO 2010/048139 A2 | 4/2010 |
| WO | WO 2010/048139 A3 | 4/2010 |
| WO | WO 2013/076509 A1 | 5/2013 |
| WO | WO 2013/138278 A1 | 9/2013 |

OTHER PUBLICATIONS

U.S. Appl. No. 15/166,527, filed May 27, 2016.
U.S. Appl. No. 15/166,511, filed May 27, 2016.
U.S. Appl. No. 15/166,549, filed May 27, 2016.
Korean Intellectual Property Office, International Search Report in International Patent Application No. PCT/US2016/034635, dated Oct. 6, 2016, 4 pp.
Korean Intellectual Property Office, Written Opinion in International Patent Application No. PCT/US2016/034635, dated Oct. 6, 2016, 8 pp.
Attayibat, et al., "Quantum chemical studies on N-donors based-pyrazole compounds as corrosion inhibitors for steel in acidic media," *Asian J. Chem*, 21(1), 2009, pp. 105-112.
Bouklah et al., "Pyridine-pyrazole compound as inhibitor for steel in 1 M HCl," *Applied Surface Science*, 240(1-4), Feb. 15, 2015, pp. 341-348.
Eddy et al., "Theoretical and experimental studies on the corrosion inhibition potentials of some purines for aluminum in 0.1 M HCl," *J. of Adv. Research*, 6(2), Jan. 20, 2014, pp. 203-217.
Li et al, "Synergistic inhibition effect of 6-benzylaminopurine and iodide ion on the corrosion of cold rolled steel in $H_3PO_4$ solution," *Corrosion Science*, 53(11), Nov. 2011, pp. 3704-3711.
Ravichandran et al., "Corrosion inhibition of brass by benzotriazole derivatives in NaCl solution," *Anti-Corrosion Methods and Materials*, 52(4), 2005, pp. 226-232.
Scendo, "Corrosion inhibition of copper by purine or adenine in sulphate solutions," *Corrosion Science*, 49(10), Oct. 2007, pp. 3953-3968.
Antonijevic et al., "Copper Corrosion Inhibitors. A review," *Int. J. Electrochem. Sci.*, 3, 2008, pp. 1-28.
Brubaker, Jr., "Metal Tetrazole Complexes: Bis-(5-aminotetrazolato)-copper(II)," Kedzie Chemical Laboratory, Michigan State University and Laboratorio De Fisica Nuclear Universidad De Chile, 82, Jun. 5, 1959, pp. 82-85.
Finšgar et al., "Inhibition of copper corrosion by 1,2,3-benzotriazole: A review," *Corrosion Science*, 52, 2010, pp. 2737-2749.
Khaled, "Studies of iron corrosion inhibition using chemical, electrochemical and computer simulation techniques," *Electrochimica Acta*, 55(22), Jun. 17, 2010, pp. 6523-6532.
Korean Intellectual Property Office, International Search Report in International Patent Application No. PCT/US2016/034629, dated Aug. 18, 2016, 4 pp.
Korean Intellectual Property Office, Written Opinion in International Patent Application No. PCT/US2016/034629, dated Aug. 18, 2016, 8 pp.
Liu et al., "Electromechanical and Quantum Chemical Studies of 5-Substituted Tetrazoles as Corrosion Inhibitors for Copper in Aerated 0.5 M $H_2SO_4$ Solution," *Materials Sciences and Applications*, 2, 2011, pp. 1268-1278.
Nalco Chemical Company, Analytical Report, "Inhibitor AZ8104," Oct. 19, 1999, 6 pp.
Nalco Chemical Company, Analytical Report, "Inhibitor AZ8104," Oct. 5, 1999, 2 pp.
Nalco Chemical Company, Analytical Report, "10% As NaCITT—Research," Oct. 19, 1999, 6 pp.
Oliphant, "Causes of Copper Corrosion in Plumbing Systems," A Review of Current Knowledge, FR/R0007, Sep. 2010, Foundation for Water Research, Bucks, U.K., 35 pp.
Pillard et al., "Toxicity of Benzotriazole and Benzotriazole Derivatives to Three Aquatic Species," *Wat. Res.* 35(2), 2001, pp. 557-560.
Scendo et al., "Adenine as an Effective Corrosion Inhibitor for Stainless Steel in Chloride Solution" *Int. J. Electrochem. Sci.*, 8, 2013, pp. 9201-9221.
Sherif, "Electrochemical and Gravimetric Study on the Corrosion and Corrosion Inhibition of Pure Copper in Sodium Chloride Solutions by Two Azole Derivatives," *Int. J. Electrochem. Sci.*, 7, 2012, pp. 1482-1495.
Solehudin, "Performance of Benzotriazole As Corrosion Inhibitors of Carbon Steel in Chloride Solution Containing Hydrogen Sulfide," *International Refereed Journal of Engineering and Science*, 1(4), Dec. 2012, pp. 21-26.

(56) References Cited

OTHER PUBLICATIONS

Téllez et al., "Coordination behavior of benzimidazole, 2-substituted benzimidazoles and benzothiazoles, towards transition metal ions," *ARKIVOC*, Issue in Honor of Prof. Rosalinda Contreras Theurel, ISSN 1551-7012, 2008, pp. 245-275.

Zhang et al., "Performance and theoretical study on corrosion inhibition of 2-(4-pyridyl)-benzimidazole for mild steel in hydrochloric acid," *Corrosion Science*, 61, Apr. 3, 2012, pp. 1-9.

European Patent Office, Extended European Search Report in European Patent Application No. 16800794.6, 8 pp. (dated Jan. 29, 2019).

European Patent Office, Extended European Search Report in European Patent Application No. 16800794.6, 8 pp. (dated Oct. 18, 2018).

Cruz-Gonzalez et al., "Adenine and guanine derivative bases of purines and their corresponding nucleosides as corrosion inhibitors in 1M hydrochloric acid," *ECS Transactions*, 36.1: 179-185 (2011).

Huynh, "The Inhibition of Copper Corrosion in Aqueous Environments With Heterocyclic Compounds," Queensland University of Technology—School of Physical Sciences, Doctor of Philosophy Thesis Examination, 99 pp. (Feb. 2004).

Khaled, "The inhibition of benzimidazole derivatives on corrosion of iron in 1 M HCl solutions," *Electrochimica Acta*, 48: 2493-2503 (2003).

Khaled et al., "Piperidines as corrosion inhibitors for iron in hydrochloric acid," *Journal of Applied Electrochemistry*, 34, 2004, pp. 697-704.

Lewis, "The Corrosion Inhibition of Copper by Benzimidazole," *Corrosion Science*, 22(6): 579-584 (1982).

Maji et al., "Corrosion inhibition of brass in presence of sulphonamidoimidazoline and hydropyrimidine in chloride solution," *Indian Journal of Chemical Technology*, vol. 16, pp. 221-227 (May 2009).

Obot et al., "Benzimidazole: Small planar molecule with diverse anti-corrosion potentials," *Journal of Molecular Liquids*, 246: 66-90 (2017).

Rehim et al., "On the corrosion inhibition of low carbon steel in concentrated sulphuric acid solutions. Part I: Chemical and electrochemical (AC and DC) studies," *Corrosion Science*, 50: 2258-2271 (2008).

Scendo, "Purine and Adenine as Corrosion Inhibitors for Copper in Acidic Chloride Solutions," Mieczyslaw; Wydawnictwo Sigma-Not (2007).

Scendo, "The Influence of Adenine on Corrosion of Copper in Chloride Solutions," *Corrosion Science*, 50(7): 2070-2077 (2008).

Shreir, "Effects of Inhibitors on Corrosion Processes," *Corrosion*, vol. 2—Corrosion Control, Newnes-Butterworths, London, England, pp. 18:38 and 18:41 (1976).

Su et al., "Corrosion Inhibition Performance of Benzimidazole N-Mannich Base for Mild Steel in Hydrochloric Acid," *Journal of Chinese Society for Corrosion and Protection*, 35(5): 415-422 (Oct. 2015).

Yanardag et al., "Corrosion Inhibition Efficiency of Benzimidazole and Benzimidazole Derivatives for Zinc, Copper and Brass," *Asian Journal of Chemistry*, 24(1): 47-52 (2012).

\* cited by examiner

WATER-SOLUBLE PYRAZOLE DERIVATIVES AS CORROSION INHIBITORS

CROSS-REFERENCE TO RELATED APPLICATION

This patent application claims the benefit of U.S. Provisional Patent Application No. 62/167,710, filed May 28, 2015, which is incorporated by reference in its entirety.

FIELD OF INVENTION

The invention relates to methods of using heterocyclic compounds as corrosion inhibitors for metal surfaces in aqueous environments.

BACKGROUND OF THE INVENTION

Copper and copper alloy components are commonly used in industrial systems due to copper's high thermal conductivity and anti-microbial properties. Copper and copper alloys (e.g., bronze and brass) are relatively resistant to corrosion as a result of protective film layers that naturally coat the surface of copper, which include an inner cuprous oxide film layer and an outer cupric oxide film layer. Under anaerobic conditions, these protective layers generally reduce the rate of further corrosion of the metal surface. However, under certain conditions, copper and copper alloys are susceptible to corrosion. In the presence of oxygen and under acidic conditions, oxidation of copper and dissolution of the copper (II) ion into water can occur.

Copper corrosion inhibitors are commonly added to industrial water systems to prevent and reduce dissolution of copper from system surfaces. In particular, the use of nitrogen-containing compounds such as azoles is well known for inhibiting the corrosion of copper and copper alloys. It is generally believed that the nitrogen lone pair electrons coordinate to the metal, resulting in the formation of a thin organic film layer that protects the copper surface from elements present in the aqueous system. Nitrogen-containing compounds such as azoles are also known to precipitate copper (II) from the aqueous solution, hindering corrosion that can occur due to galvanic reactions between copper and other metals.

Oxidizing halogens are commonly used as biocides in industrial systems to control slime and microbiological growth in water. The protective film provided by many azoles erodes in the presence of oxidizing halogens such as chlorine, hypochlorite, and hypobromite, reducing the effectiveness of the corrosion inhibitor. Moreover, a decrease in copper (II) precipitation often occurs in the presence of oxidizing halogens due to halogen attack of the corrosion inhibitor in solution. Thus, in the presence of oxidizing halogens, an excess or continuous injection of corrosion inhibitor is often required to maintain the organic protective film.

A serious concern in the industry is the environmental pollution caused by introduction of toxic corrosion inhibitors into the environment. While many heterocyclic compounds have found wide application as corrosion inhibitors, many commonly used anti-corrosive agents such as benzotriazole and its derivatives are non-biodegradable and toxic. The industry is steadily moving toward the development of environmentally-friendly corrosion inhibitors that provide excellent inhibitory activity while having both non-toxic and biodegradable properties.

An environmentally-friendly method of inhibiting metal corrosion would be beneficial to the industry. Moreover, it would be desirable to provide a method that provides protection of copper in the absence and presence of oxidizing halogen agents.

BRIEF SUMMARY OF THE INVENTION

In an embodiment, the invention provides a method for inhibiting corrosion of a metal surface in contact with an aqueous system. The method comprises adding to the aqueous system a compound of formula (I),

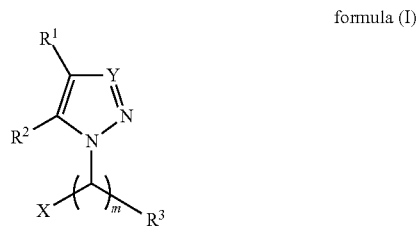

formula (I)

wherein X is selected from the group consisting of —OH, —$NH_2$, —SH, and halogen;

Y is selected from the group consisting of —$CR^4$ and nitrogen;

$R^1$ and $R^2$ form a six-membered aromatic ring, or each of $R^1$ and $R^2$ is the same or different and selected from the group consisting of hydrogen, aryl, heteroaryl, $C_1$-$C_{16}$ alkyl, $C_2$-$C_{16}$ alkenyl, $C_2$-$C_{16}$ alkynyl, $C_3$-$C_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl;

$R^3$ is selected from the group consisting of hydrogen, aryl, heteroaryl, $C_1$-$C_{16}$ alkyl, $C_2$-$C_{16}$ alkenyl, $C_2$-$C_{16}$ alkynyl, $C_3$-$C_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl;

$R^4$ is selected from the group consisting of hydrogen, aryl, heteroaryl, $C_1$-$C_{16}$ alkyl, $C_2$-$C_{16}$ alkenyl, $C_2$-$C_{16}$ alkynyl, $C_3$-$C_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl; and m is an integer of from 1 to 9; or a salt thereof.

In another embodiment, the invention provides a method for inhibiting corrosion of a metal surface in contact with an aqueous system comprising an oxidizing halogen compound. The method comprises adding to the aqueous system a compound of formula (II),

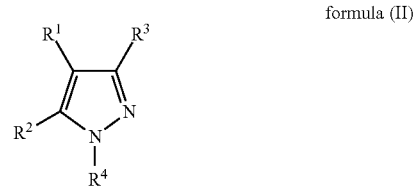

formula (II)

wherein each of $R^1$, $R^2$, and $R^3$ is the same or different and selected from the group consisting of hydrogen, aryl, heteroaryl, $C_1$-$C_{16}$ alkyl, $C_2$-$C_{16}$ alkenyl, $C_2$-$C_{16}$ alkynyl, $C_3$-$C_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl; and $R^4$ is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl; or.

a salt thereof.

In another embodiment, the invention provides a formulation for inhibiting corrosion of a metal surface in contact with an aqueous system. The formulation comprises a compound of formula (I) or (II), a phosphoric acid, and a phosphinosuccinic oligomer.

In another embodiment, the invention provides a compound of formula (I),

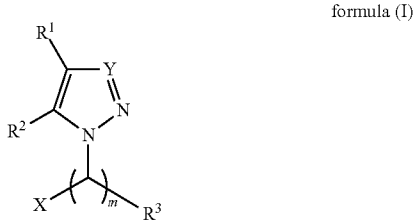

formula (I)

wherein X is selected from the group consisting of —OH, —NH$_2$, and —SH;

Y is selected from the group consisting of —CR$^4$ and nitrogen;

$R^1$ and $R^2$ form a six-membered aromatic ring or each of $R^1$ and $R^2$ is the same or different and selected from the group consisting of hydrogen, aryl, heteroaryl, $C_1$-$C_{16}$ alkyl, $C_2$-$C_{16}$ alkenyl, $C_2$-$C_{16}$ alkynyl, $C_3$-$C_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl;

$R^3$ is selected from the group consisting of aryl, heteroaryl $C_2$-$C_{16}$ alkenyl, $C_2$-$C_{16}$ alkynyl, $C_3$-$C_8$ cycloalkyl, benzyl, alkylheteroaryl, halogen, cyano, alkoxy, thiol, alkylthio, phosphoryl, phosphonyl, and sulfonyl;

$R^4$ is selected from the group consisting of hydrogen, aryl, heteroaryl, $C_1$-$C_{16}$ alkyl, $C_2$-$C_{16}$ alkenyl, $C_2$-$C_{16}$ alkynyl, $C_3$-$C_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl; and m is 1; or wherein X is selected from the group consisting of —OH, —NH$_2$, and —SH;

Y is —CR$^4$;

$R^1$ is selected from the group consisting of hydrogen, $C_1$-$C_{16}$ alkyl, $C_2$-$C_{16}$ alkenyl, $C_2$-$C_{16}$ alkynyl, aryl, heteroaryl, $C_3$-$C_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl;

$R^2$ is selected from the group consisting of $C_1$-$C_{16}$ alkyl, $C_2$-$C_{16}$ alkenyl, $C_2$-$C_{16}$ alkynyl, aryl, heteroaryl, $C_3$-$C_8$ cycloalkyl, benzyl, alkylheteroaryl, halosubstituted alkyl, amino, aminoalkyl, cyano, hydroxyl, alkoxy, thiol, alkylthio, carbonyl, nitro, phosphoryl, phosphonyl, and sulfonyl;

$R^3$ is $C_1$-$C_{16}$ alkyl;

$R^4$ is selected from the group consisting of hydrogen, $C_1$-$C_{16}$ alkyl, $C_2$-$C_{16}$ alkenyl, $C_2$-$C_{16}$ alkynyl, aryl, heteroaryl, $C_3$-$C_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl; and m is 1; or a salt thereof.

DETAILED DESCRIPTION OF THE INVENTION

Figure 1:
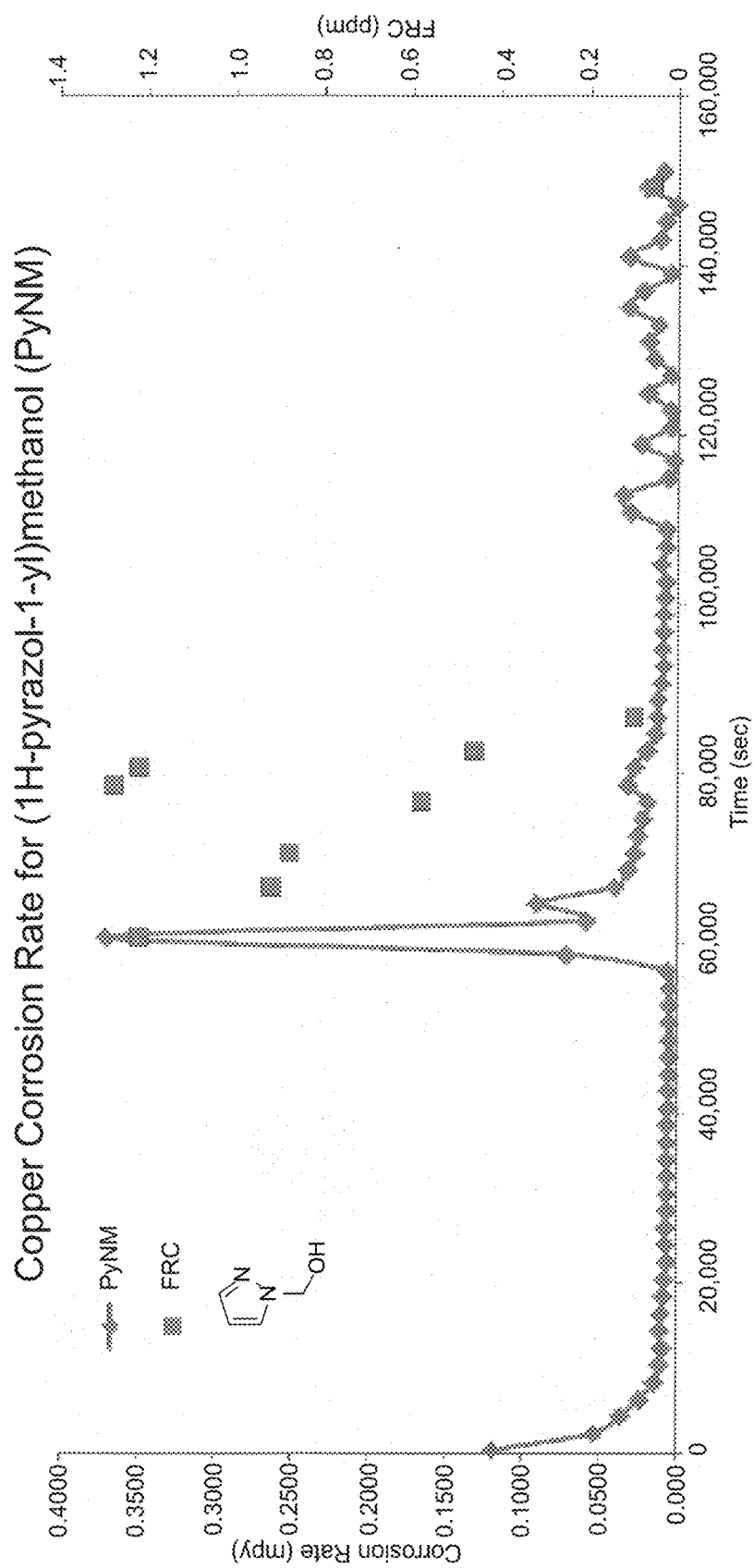
FIG. 1 is a line graph that illustrates the corrosion rate of copper using (1H-pyrazol-1-yl)methanol as a corrosion inhibitor in the absence and presence of bleach.

The following definitions are provided to determine how terms used in this application, and in particular, how the claims are to be construed. The organization of the definitions is for convenience only and is not intended to limit any of the definitions to any particular category.

"Alkoxy" refers to a moiety of the formula RO—, where R is alkyl, alkenyl, or alkynyl;

"Alkyl" refers to a straight-chain or branched alkyl substituent. Examples of such substituents include methyl, ethyl, propyl, isopropyl, n-butyl, sec-butyl, isobutyl, tert-butyl, pentyl, isoamyl, hexyl, and the like;

"Alkylheteroaryl" refers to an alkyl group linked to a heteroaryl group;

"Alkenyl" refers to a straight or branched hydrocarbon, preferably having 2, 3, 4, 5, 6, 7, 8, 9, 10, 11, 12, 13, 14, 15, or 16 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents;

"Alkylthio" refers to a moiety of the formula RS—, where R is alkyl, aryl, alkenyl, or alkynyl;

"Alkynyl" refers to a straight or branched hydrocarbon, preferably having 2, 3, 4, 5, 6, 7, 8, 9, 10, 11, 12, 13, 14, 15, or 16 carbons, and having one or more carbon-carbon triple bonds. Alkynyl groups include, but are not limited to, ethynyl, propynyl, and butynyl. Alkynyl groups may be unsubstituted or substituted by one or more suitable substituents;

"Amino" refers to the moiety H₂N—;

"Aminoalkyl" refers to a nitrogen substituent attached to one or more carbon groups, such as alkyl or aryl. For example, the aminoalkyl group can be RHN— (secondary) or R₂N— (tertiary) where R is alkyl or aryl;

"Aqueous system" refers to any system containing metal components which are in contact with water on a periodic or continuous basis;

"Aryl" refers to an unsubstituted or substituted aromatic carbocyclic substituent, as commonly understood in the art, and the term "$C_6$-$C_{10}$ aryl" includes phenyl, naphthyl, and anthracyl. It is understood that the term aryl applies to cyclic substituents that are planar and comprise 4n+2n electrons, according to Hückel's Rule;

"Carbonyl" refers to a substituent comprising a carbon double bonded to an oxygen. Examples of such substituents include aldehydes, ketones, carboxylic acids, esters, amides, and carbamates;

"Cycloalkyl" refers to a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups such as methyl groups, ethyl groups, and the like;

"Halogen" or "halo" refers to F, Cl, Br, and I;

"Halosubstituted alkyl" refers to an alkyl group as described above substituted with one or more halogens, for example, chloromethyl, trifluoromethyl, 2,2,2-trichloroethyl, and the like;

"Heteroaryl" refers to a monocyclic or bicyclic 5- or 6-membered ring system, wherein the heteroaryl group is unsaturated and satisfies Htickel's rule. Non-limiting examples of heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like;

"Industrial water system" means any system that circulates water as its primary ingredient. Nonlimiting examples of "industrial water systems" include cooling systems, boiler systems, heating systems, membrane systems, paper making process or any other system that circulates water as defined below;

"Oxidizing halogen" refers to an oxidizing agent comprising at least one halogen. Examples of oxidizing halogens include, but are not limited to, chlorine bleach, chlorine, bromine, iodine, hypochlorite, hypobromite, iodine/hypoiodous acid, hypobromous acid, halogenated hydantoins, chlorine dioxide, stabilized versions of hypochlorous or hypobromous acids, and compounds or chemical groups capable of releasing chlorine, bromine, or iodine;

"Mild steel" refers to carbon and low alloy steels;

"Water" means any substance that has water as a primary ingredient. Water may include pure water, tap water, fresh water, recycled water, brine, steam, and/or any aqueous solution, or aqueous blend;

"Water soluble" means materials that are soluble in water to at least about 5%, by weight, at 25° C.

For convenience of reference herein, the structure of the compounds of formula (I) is numbered as follows:

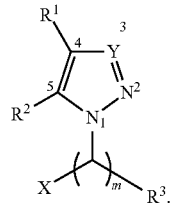

formula (I)

For convenience of reference herein, the structure of the compounds of formula (II) is numbered as follows:

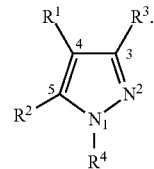

formula (II)

Whenever a range of the number of atoms in a structure is indicated (e.g., a $C_1$-$C_{16}$ alkyl, $C_2$-$C_{16}$ alkenyl, $C_2$-$C_{16}$ alkynyl, etc.), it is specifically contemplated that any sub-range or individual number of carbon atoms falling within the indicated range also can be used. Thus, for instance, the recitation of a range of 1-16 carbon atoms (e.g., $C_1$-$C_{16}$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-16 carbon atoms (e.g., $C_2$-$C_{16}$) as used with respect to any chemical group (e.g., alkyl) referenced herein encompasses and specifically describes 1, 2, 3, 4, 5, 6, 7, 8, 9, 10, 11, 12, 13, 14, 15, and/or 16 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 1-13 carbon atoms, 1-14 carbon atoms, 1-15 carbon atoms, 1-16 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 2-13 carbon atoms, 2-14 carbon atoms, 2-15 carbon atoms, 2-16 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 3-13 carbon atoms, 3-14 carbon atoms, 3-15 carbon atoms, 3-16 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, 4-12 carbon atoms, 4-13 carbon atoms, 4-14 carbon atoms, 4-15 carbon atoms, and/or 4-16 carbon atoms, etc., as appropriate).

The invention provides methods of using heterocyclic compounds, novel heterocyclic compounds, and formulations that are particularly useful for inhibiting corrosion of metallic components in industrial water systems. The methods of the present invention employ compounds of relatively low acute toxicity to aquatic organisms, presenting a more environmentally friendly alternative to existing methods. Applicants have discovered that pyrazole compounds substituted with a heteroatom-containing alkyl group at the 1-position have increased water-solubility. The water-soluble pyrazoles of the present methods provide excellent metal corrosion resistance when added to an aqueous system in contact with a metal surface. While pyrazole provides poor protection against corrosion of copper, (1H-pyrazol-1-yl)methanol provides excellent copper corrosion resistance (0.4232 mpy vs. 0.0057 mpy).

Applicants have also surprisingly and unexpectedly discovered that pyrazole derivatives of the present methods have exemplary stability in the presence of oxidizing halogen compounds. While not wishing to be bound by any particular theory, it is believed that the pyrazole derivatives of the present methods provide a protective film that is impenetrable or essentially impenetrable to common oxidizing halogen compounds. Thus, in certain embodiments, methods of the present invention provide protection against metal corrosion in aqueous systems which employ oxidizing halogen compounds as biocides.

In an embodiment, the invention provides a method for inhibiting corrosion of a metal surface in contact with an aqueous system. The method comprises adding to the aqueous system a compound of formula (I),

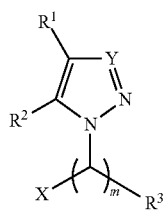

formula (I)

wherein X is selected from the group consisting of —OH, —NH$_2$, —SH, and halogen;

Y is selected from the group consisting of —CR$^4$ and nitrogen;

R$^1$ and R$^2$ form a six-membered aromatic ring, or each of R$^1$ and R$^2$ is the same or different and selected from the group consisting of hydrogen, aryl, heteroaryl, C$_1$-C$_{16}$ alkyl, C$_2$-C$_{16}$ alkenyl, C$_2$-C$_{16}$ alkynyl, C$_3$-C$_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl;

R$^3$ is selected from the group consisting of hydrogen, aryl, heteroaryl, C$_1$-C$_{16}$ alkyl, C$_2$-C$_{16}$ alkenyl, C$_2$-C$_{16}$ alkynyl, C$_3$-C$_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl;

R$^4$ is selected from the group consisting of hydrogen, aryl, heteroaryl, C$_1$-C$_{16}$ alkyl, C$_2$-C$_{16}$ alkenyl, C$_2$-C$_{16}$ alkynyl, C$_3$-C$_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl; and m is an integer of from 1 to 9; or a salt thereof.

In certain preferred embodiments, X is —OH.

In certain preferred embodiments, Y is —CR$^4$, where R$^4$ is hydrogen.

In certain preferred embodiments, Y is —CR$^4$, where R$^4$ is phenyl.

In certain preferred embodiments, Y is —CR$^4$, where R$^4$ is methyl.

In certain preferred embodiments, R$^1$ and R$^2$ are hydrogen.

In certain preferred embodiments, R$^3$ is hydrogen.

In certain preferred embodiments, R$^3$ is methyl.

In certain preferred embodiments, R$^3$ is phenyl.

In certain preferred embodiments, R$^1$ is methyl and Y is —CR$^4$, where R$^4$ is methyl.

In certain preferred embodiments, R$^1$ is methyl and R$^2$ is hydrogen.

In certain preferred embodiments, m is 1.

In certain preferred embodiments, the compound of formula (I) is

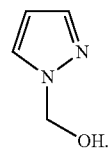

In certain preferred embodiments, the compound of formula (I) is

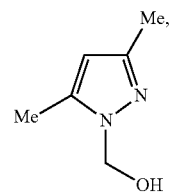

wherein Me is methyl.

In certain preferred embodiments, the compound of formula (I) is

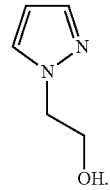

In certain preferred embodiments, the compound of formula (I) is

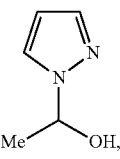

wherein Me is methyl.

In certain preferred embodiments, the compound of formula (I) is

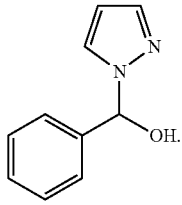 [SMILES: OC(c1ccccc1)n1cccn1]

In certain preferred embodiments, the compound of formula (I) is

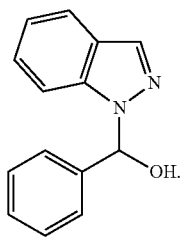 [SMILES: OC(c1ccccc1)n1ncc2ccccc21]

In certain preferred embodiments, the compound of formula (I) is

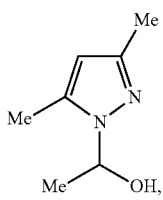

wherein Me is methyl.

In certain preferred embodiments, the compound of formula (I) is

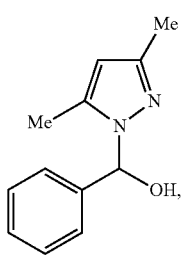

wherein Me is methyl.

When $R^1$ and $R^2$ form a six-membered aromatic ring, the aromatic ring is optionally substituted and has the following structure:

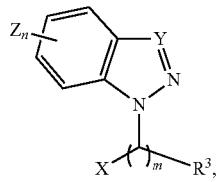

wherein each of Z is the same or different, and is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl; X is selected from the group consisting of —OH, —$NH_2$, —SH, and halogen; Y is selected from the group consisting of —$CR^4$ and nitrogen; m is an integer of from 1 to 9; and n is 1, 2, 3, or 4; or a salt thereof. $R^1$-$R^4$ are defined as shown above.

The compounds of formula (I) can be a single enantiomer (i.e., (R)-isomer or (S)-isomer), a racemate, or a mixture of enantiomers at any ratio.

The compounds of formula (I) can be prepared by any suitable synthetic chemical method. One method of preparation is a one-step synthesis using commercially available materials. A pyrazole compound undergoes a condensation reaction with an aldehyde to form the 1-substituted pyrazole compound. For example, 3,5-dimethylpyrazole reacts with formaldehyde to form (3,5-dimethyl-1H-pyrazol-1-yl) methanol.

In another embodiment, the invention provides a method for inhibiting corrosion of a metal surface in contact with an aqueous system comprising an oxidizing halogen compound. The method comprises adding to the aqueous system a compound of formula (II), formula (II)

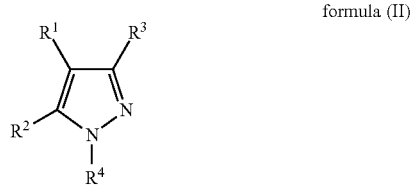

wherein each of $R^1$, $R^2$, and $R^3$ is the same or different and selected from the group consisting of hydrogen, aryl, heteroaryl, $C_1$-$C_{16}$ alkyl, $C_2$-$C_{16}$ alkenyl, $C_2$-$C_{16}$ alkynyl, $C_3$-$C_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl; and $R^4$ is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl; or a salt thereof.

In certain preferred embodiments, $R^1$ and $R^3$ are $C_1$-$C_{16}$ alkyl.

In certain preferred embodiments, $R^1$ and $R^3$ are methyl.

In certain preferred embodiments, $R^3$ is a halogen.

In certain preferred embodiments, $R^3$ is a chloride.

In certain preferred embodiments, $R^4$ is hydrogen.

In certain preferred embodiments, the compound of formula (II) is

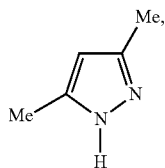

wherein Me is methyl.

In certain preferred embodiments, the compound of formula (II) is

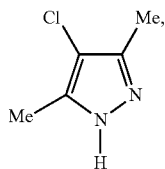

wherein Me is methyl.

In certain preferred embodiments, the compound of formula (II) is

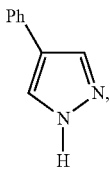

wherein Ph is phenyl.

In certain preferred embodiments, $R^4$ is hydrogen. While not wishing to be bound by any particular theory, it is postulated that when $R^4$ is hydrogen, hydrogen-bonding can occur between molecules when added to an aqueous system in contact with a metal surface, thereby resulting in enhanced strength of the corrosion inhibitor protective film on the metal surface. Moreover, compounds of formula (II) where $R^4$ is hydrogen generally have increased water solubility.

The compounds of formulae (I) and (II) may provide corrosion protection for any metal or metal alloy including, but not limited to, copper, iron, silver, steel (e.g., galvanized steel), and aluminum. In certain preferred embodiments, a compound of formula (I) or (II) is added to an aqueous system in contact with a metal surface comprising copper to inhibit metal corrosion. In certain preferred embodiments, a compound of formula (I) or (II) is added to an aqueous system in contact with a metal surface comprising a copper alloy to inhibit metal corrosion. In certain embodiments, copper complexes with one or more heteroatoms in a compound of formula (I) or (II). Copper has a wide-range of applications, including use as copper piping and tubing in plumbing and industrial machinery. Copper and copper alloys are well known for their use in cooling water and boiler water systems.

The compounds of formulae (I) and (II) can be used to protect any copper alloy, including bronze, copper-nickel, and brass. Bronze commonly comprises copper and tin, but may comprise other elements including aluminum, manganese, silicon, arsenic, and phosphorus. Brass comprises copper and zinc, and is commonly used in piping in water boiler systems. In certain embodiments, a compound of formula (I) or (II) is added to an aqueous system in contact with a metal surface comprising bronze to inhibit metal corrosion. In certain preferred embodiments, a compound of formula (I) or (II) is added to an aqueous system in contact with a metal surface comprising brass (e.g., admirality brass) to inhibit metal corrosion. In certain preferred embodiments, a compound of formula (I) or (II) is added to an aqueous system in contact with a metal surface comprising a copper-nickel alloy to inhibit metal corrosion.

In certain embodiments, a compound of formula (I) or (II) inhibits the corrosion of mild steel. In certain embodiments, a compound of formula (I) or (II) inhibits the corrosion of metal alloys including, but not limited to, galvanized steel, stainless steel, cast iron, nickel, and combinations thereof. While not wishing to be bound by any particular theory, it is postulated that the compounds of formulae (I) and (II) inactivate Cu (II) in solution, preventing the occurrence of galvanic cells on the steel surface. Thus, in certain embodiments, a compound of formula (I) or (II) inhibits pitting corrosion of mild steel.

The corrosion rate provided by compounds of formulae (I) and (II) is not limited. In certain embodiments, a method of inhibiting corrosion comprising using a compound of formula (I) or (II) provides a metal corrosion rate that is acceptable according to industry standards, e.g., about 0.2 mpy or less. In certain preferred embodiments, a compound of formula (I) or (II) provides a metal corrosion rate of about 0.1 mpy or less. Thus, in certain preferred embodiments, a compound of formula (I) or (II) provides a metal corrosion rate of about 0.1 mpy or less, about 0.05 mpy or less, about 0.04 mpy or less, about 0.03 mpy or less, about 0.02 mpy or less, about 0.01 mpy or less, about 0.005 mpy or less, or about 0.002 mpy or less.

While compounds of formulae (I) and (II) can be added to an aqueous system at any dosage rate, the compounds of formulae (I) and (II) are generally added to an aqueous system at a dosage rate of from about 0.01 ppm to about 500 ppm. In certain embodiments, a compound of formula (I) or (II) is added to an aqueous system at a dosage rate of from about 0.01 ppm to about 100 ppm. Thus, in certain preferred embodiments, a compound of formula (I) or (II) is added to an aqueous system at a dosage rate of from about 0.01 ppm to about 100 ppm, from about 0.01 ppm to about 75 ppm, from about 0.01 ppm to about 50 ppm, from about 0.01 ppm to about 25 ppm, from about 0.01 ppm to about 10 ppm, from about 0.01 ppm to about 5 ppm, from about 0.1 ppm to about 100 ppm, from about 0.1 ppm to about 75 ppm, from about 0.1 ppm to about 50 ppm, from about 0.1 ppm to about 25 ppm, from about 0.1 ppm to about 10 ppm, from about 0.1 ppm to about 5 ppm, from about 1 ppm to about 100 ppm, from about 1 ppm to about 75 ppm, from about 1 ppm to about 50 ppm, from about 1 ppm to about 25 ppm, from about 1 ppm to about 10 ppm, from about 5 ppm to about 100 ppm, from about 10 ppm to about 100 ppm, from about 25 ppm to about 100 ppm, from about 50 ppm to about 100 ppm, or from about 80 ppm to about 100 ppm.

An advantage of the present methods is that the compounds of formulae (I) and (II) can be formulated at any pH, including at neutral pH. This is in contrast to many existing methods that employ corrosion inhibitors such as benzotriazole, which require formulation at more hazardous pH levels (e.g., basic pH). Moreover, the compounds of formulae (I) and (II) can be used to inhibit corrosion of metal in an aqueous system having any pH. In certain preferred embodiments, a compound of formula (I) or (II) is added to an aqueous system having a pH of from about 2 to about 12. Thus, in certain preferred embodiments, a compound of formula (I) or (II) is added to an aqueous system having a pH of from about 2 to about 12, from about 3 to about 12, from about 4 to about 12, from about 5 to about 12, from about 6 to about 12, from about 2 to about 11, from about 2 to about 10, from about 2 to about 9, from about 2 to about 8, from about 2 to about 7, from about 2 to about 6, from about 2 to about 5, from about 6 to about 9, from about 6 to about 8, from about 7 to about 12, from about 8 to about 12, from about 9 to about 12, from about 7 to about 10, or from about 8 to about 10.

Another advantage of the present methods is that the compounds of formulae (I) and (II) provide corrosion protection for metal surfaces in the presence of oxidizing halogens. In certain preferred embodiments, a compound of formula (I) or (II) is added to an aqueous system in contact with a metal surface and inhibits corrosion of the metal surface in the presence of any oxidizing halogen compound. In certain preferred embodiments, a compound of formula (I) or (II) inhibits metal corrosion in the presence of oxidizing halogen compounds including, but not limited to, hypochlorite bleach, chlorine, bromine, hypochlorite, hypobromite, chlorine dioxide, iodine/hypoiodous acid, hypobromous acid, halogenated hydantoins, stabilized versions of hypochlorous or hypobromous acids, or combinations thereof. While not wishing to be bound by any particular theory, it is postulated that the relatively large number of heteroatoms of the compounds of formulae (I) and (II) provide a greater number of sites for bonding to metal surfaces and metal ions, which can provide enhanced corrosion inhibition as compared to many existing corrosion inhibitors. In addition, it is postulated that compounds of formula (I) can form stable films due in part to the formation of a chelation complex with the metal surface.

As discussed above, the compounds of formulae (I) and (II) can reduce the rate of corrosion of copper. In certain embodiments, a compound of formula (I) or (II) surprisingly and unexpectedly provides lower corrosion rates for copper in the presence of oxidizing halogen compounds than compounds commonly used as corrosion inhibitors, such as tolyltriazole. In certain embodiments, a compound of formula (I) or (II) provides a metal corrosion rate in the presence of an oxidizing halogen compound of about 0.2 mpy or less. In certain preferred embodiments, a compound of formula (I) or (II) provides a metal corrosion rate in the presence of an oxidizing halogen compound of about 0.1 mpy or less. Thus, in certain preferred embodiments, a compound of formula (I) or (II) provides a metal corrosion rate in the presence of an oxidizing halogen compound of about 0.1 mpy or less, about 0.05 mpy or less, about 0.04 mpy or less, about 0.03 mpy or less, about 0.02 mpy or less, about 0.01 mpy or less, about 0.005 mpy or less, or about 0.002 mpy or less. In certain preferred embodiments, the metal corrosion rate provided by a compound of formula (I) or (II) is essentially the same in the absence or presence of an oxidizing compound.

In certain preferred embodiments, a compound of formula (I) or (II) inhibits corrosion of copper in the presence of oxidizing halogen compounds including, but not limited to, hypochlorite bleach, chlorine, bromine, hypochlorite, hypobromite, chlorine dioxide, iodine/hypoiodous acid, hypobromous acid, halogenated hydantoins, stabilized versions of hypochlorous or hypobromous acids, or combinations thereof.

In certain embodiments, a compound of formula (I) or (II) inhibits metal corrosion when added to an aqueous system comprising a non-halogen-containing oxidizing biocide including, but not limited to, peroxides (e.g., hydrogen peroxide), persulfates, permanganates, and peracetic acids.

Another advantage of the present methods is that a smaller amount of oxidizing halogen compound is required to maintain low microbial levels because the compounds of formulae (I) and (II) generally has reduced interaction with the oxidizing halogen compound. Furthermore, halogenated azoles that result from the reaction between an azole and oxidizing agent are known to be environmentally undesirable due to their toxicity. Thus, another advantage of the present methods is that the compounds of formulae (I) and (II) are resistant or essentially resistant to halogen attack, and do not lead to the release of halogenated azoles into the environment.

Another advantage of the present invention is that the compounds of formula (I) have enhanced water solubility. In certain embodiments, a compound of formula (I) is water-soluble. In certain preferred embodiments, a compound of formula (I) is soluble in water of from about 70% to about >99% by weight, at 25° C. In other words, in certain embodiments, about 70% to about >99% of a compound of formula (I) dissolves in water at 25° C. Thus, in certain preferred embodiments, a compound of formula (I) is soluble in water of from about 70% to about >99%, from about 75% to about >99%, from about 80% to about >99%, from about 85% to about >99%, from about 90% to about >99%, from about 95% to about >99%, or from about 98% to about >99%, at 25° C. In certain embodiments, >99% of a compound of formula (I) is soluble in water.

In certain preferred embodiments, the aqueous system is a cooling water system. The cooling water system can be a closed loop cooling water system or an open loop cooling water system. In certain preferred embodiments, a compound of formula (I) or (II) is added to a closed loop cooling water system at a dosage rate of from about 0.01 ppm to about 200 ppm. In certain preferred embodiments, a compound of formula (I) or (II) is added to an open loop cooling water system at a dosage rate of from about 0.01 ppm to about 20 ppm.

The compounds of formulae (I) and (II) are contacted with a metal surface by any suitable method. In certain embodiments, a solution of a compound of formula (I) or (II) is contacted with a metal surface by immersion, spraying, or other coating techniques. In certain preferred embodiments, a solution of a compound of formula (I) or (II) is introduced into the water of the aqueous system by any conventional method and is fed into the aqueous system on either a periodic or continuous basis.

In certain embodiments, if a compound of formula (I) or (II) is relatively insoluble in water, the compound may be made soluble by forming an organic or inorganic salt of the compound. Thus, in certain embodiments, a compound of formula (I) or (II) is a water-soluble salt. In certain embodiments, a compound of formula (I) or (II) is added as a solution in a water-miscible co-solvent including, but not limited to, acetone, methanol, ethanol, propanol, formic acid, formamide, propylene glycol, or ethylene glycol. In certain embodiments, low molecular weight polyethylene glycol, polypropylene glycol, or a surfactant is used to increase the solubility of a compound of formula (I) or (II). In certain embodiments, a co-solvent is used to achieve maximum solubility of a compound of formula (I) or (II) in the aqueous system.

In another embodiment, the invention provides a formulation for inhibiting corrosion of a metal surface in contact with an aqueous system. The formulation comprises a compound of formula (I) or (II), a phosphoric acid, and a phosphinosuccinic oligomer. In a certain preferred embodiments, the phosphoric acid is orthophosphoric acid (i.e., phosphoric acid). In certain embodiments, the phosphinosuccinic oligomer is selected from the phosphinosuccinic oligomers as disclosed in U.S. Pat. No. 6,572,789, which is hereby incorporated by reference.

In certain preferred embodiments, the formulation comprises a compound of formula (I) wherein X is selected from the group consisting of —OH, —NH$_2$, —SH, and halogen; Y is selected from the group consisting of —CR$^4$ and nitrogen; R$^1$ and R$^2$ form a six-membered aromatic ring, or each of R$^1$ and R$^2$ is the same or different and selected from the group consisting of hydrogen, aryl, heteroaryl, C$_1$-C$_{16}$ alkyl, C$_2$-C$_{16}$ alkenyl, C$_2$-C$_{16}$ alkynyl, C$_3$-C$_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl; R$^3$ is selected from the group consisting of hydrogen, aryl, heteroaryl, C$_1$-C$_{16}$ alkyl, C$_2$-C$_{16}$ alkenyl, C$_2$-C$_{16}$ alkynyl, C$_3$-C$_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl; R$^4$ is selected from the group consisting of hydrogen, aryl, heteroaryl, C$_1$-C$_{16}$ alkyl, C$_2$-C$_{16}$ alkenyl, C$_2$-C$_{16}$ alkynyl, C$_3$-C$_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl; and m is an integer of from 1 to 9; or a salt thereof.

In certain preferred embodiments, the formulation comprises a compound of formula (II) wherein each of R$^1$, R$^2$, and R$^3$ is the same or different and selected from the group consisting of hydrogen, aryl, heteroaryl, C$_1$-C$_{16}$ alkyl, C$_2$-C$_{16}$ alkenyl, C$_2$-C$_{16}$ alkynyl, C$_3$-C$_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl; and R$^4$ is selected from the group consisting of hydrogen, deuterium, C$_1$-C$_{16}$ alkyl, aryl, C$_2$-C$_{16}$ alkenyl, C$_2$-C$_{16}$ alkynyl, heteroaryl, C$_3$-C$_8$ cycloalkyl, benzyl, alkylheteroaryl, halogen, hydroxyl, and carbonyl; or a salt thereof.

In certain embodiments, the formulation further comprises a fluorescent organic compound. In certain preferred embodiments, the fluorescent organic compound is selected from the group consisting of Rhodamine, a derivative of Rhodamine, an acridine dye, fluorescein, a derivative of fluorescein, and combinations thereof. In certain embodiments, the formulation further comprises a fluorescent tagged polymer.

In certain embodiments, the formulation has a pH of from about 2 to about 5. Thus, in certain embodiments, the formulation has a pH of from about 2 to about 5, from about 2 to about 4, from about 2 to about 3, or from about 3 to about 5. In certain embodiments, the formulation has a pH of from about 11 to about 14. Thus, in certain embodiments, the formulation has a pH of from about 11 to about 14, from about 11 to about 13, from about 12 to about 14, or from about 13 to about 14.

In another embodiment, the invention provides a compound of formula (I):

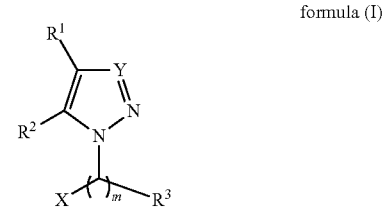

formula (I)

wherein X is selected from the group consisting of —OH, —NH$_2$, and —SH;

Y is selected from the group consisting of —CR$^4$ and nitrogen;

R$^1$ and R$^2$ form a six-membered aromatic ring or each of R$^1$ and R$^2$ is the same or different and selected from the group consisting of hydrogen, aryl, heteroaryl, C$_1$-C$_{16}$ alkyl, C$_2$-C$_{16}$ alkenyl, C$_2$-C$_{16}$ alkynyl, C$_3$-C$_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl;

R$^3$ is selected from the group consisting of aryl, heteroaryl C$_2$-C$_{16}$ alkenyl, C$_2$-C$_{16}$ alkynyl, C$_3$-C$_8$ cycloalkyl, benzyl, alkylheteroaryl, halogen, cyano, alkoxy, thiol, alkylthio, phosphoryl, phosphonyl, and sulfonyl;

R$^4$ is selected from the group consisting of hydrogen, aryl, heteroaryl, C$_1$-C$_{16}$ alkyl, C$_2$-C$_{16}$ alkenyl, C$_2$-C$_{16}$ alkynyl, C$_3$-C$_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl; and m is 1; or wherein X is selected from the group consisting of —OH, —NH$_2$, and —SH;

Y is —CR$^4$;

R$^1$ is selected from the group consisting of hydrogen, C$_1$-C$_{16}$ alkyl, C$_2$-C$_{16}$ alkenyl, C$_2$-C$_{16}$ alkynyl, aryl, heteroaryl, C$_3$-C$_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl;

R$^2$ is selected from the group consisting of C$_1$-C$_{16}$ alkyl, C$_2$-C$_{16}$ alkenyl, C$_2$-C$_{16}$ alkynyl, aryl, heteroaryl, C$_3$-C$_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl;

R$^3$ is C$_1$-C$_{16}$ alkyl;

R$^4$ is selected from the group consisting of hydrogen, C$_1$-C$_{16}$ alkyl, C$_2$-C$_{16}$ alkenyl, C$_2$-C$_{16}$ alkynyl, aryl, heteroaryl, C$_3$-C$_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl; and m is 1; or a salt thereof.

In certain preferred embodiments, R$^3$ is aryl or heteroaryl.

In certain preferred embodiments, the compound of formula (I) is

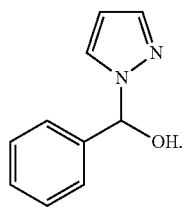 [SMILES: OC(c1ccccc1)n1cccn1]

In certain preferred embodiments, the compound of formula (I) is

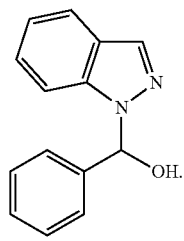 [SMILES: OC(c1ccccc1)n1ncc2ccccc21]

In certain preferred embodiments, the compound of formula (I) is

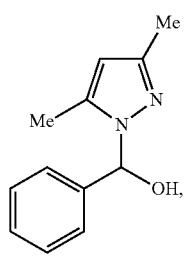

wherein Me is methyl.

In certain preferred embodiments, the compound of formula (I) is

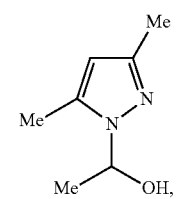

wherein Me is methyl.

Those skilled in the art will appreciate that compounds of formula (I) or (II) can be added to an aqueous system alone or in combination with other corrosion inhibitors or treatment chemicals. Multiple corrosion inhibitors can be dosed as a combined corrosion inhibitor formulation or each corrosion inhibitor can be added separately, including two or more compounds of formula (I) and/or formula (II). Moreover, a compound of formula (I) or (II) can be added to an aqueous system in combination with a variety of additional corrosion inhibitors including, but not limited to, triazoles, benzotriazoles (e.g., benzotriazole or tolyltriazole), benzimidazoles, orthophosphate, polyphosphates, phosphonates, molybdates, silicates, oximes, and nitrites. The compounds of formulae (I) and (II) also can be added to an aqueous system in combination with a variety of additional additives, such as treatment polymers, anti-microbial agents, anti-scaling agents, colorants, fillers, buffers, surfactants, viscosity modifiers, chelating agents, dispersants, deodorants, masking agents, oxygen scavengers, indicator dyes, and combinations thereof.

The compounds of formulae (I) and (II) can be added to an aqueous system in any form. In certain embodiments, a compound of formula (I) or (II) is added to an aqueous system as a dried solid. In certain embodiments, a compound of formula (I) or (II) is added to an aqueous system as a solution in a co-solvent miscible with water. In certain preferred embodiments, a compound of formula (I) or (II) is added to an aqueous system as an aqueous solution.

In certain embodiments, the present invention provides methods of low aquatic toxicity. In certain embodiments, a compound of formulae (I) and (II) has reduced toxicity. In certain embodiments, a compound of formula (I) or (II) has a $LC_{50}$ of greater than 100 mg/L. In certain embodiments, a compound of formula (I) or (II) has a $LC_{50}$ of greater than 100 mg/L in a *Oncorhynchus mykiss* aquatic toxicity test.

In certain embodiments, a compound of formula (I) is added to a laundry system or a warewashing system.

In certain embodiments, a compound of formula (I) or (II) is added to an aqueous system that recirculates water. In certain embodiments, a compound of formula (I) or (II) is added to an aqueous system that has stagnant water.

The following examples further illustrate the invention but, of course, should not be construed as in any way limiting its scope.

EXAMPLE 1

This Example illustrates a method of synthesizing compounds of formulae (I) and (II) in accordance with an embodiment of the present invention.

General Chemistry Methods. The reactions were performed under positive pressure of nitrogen with oven-dried glassware. Pyrazole and 3,5-dimethylpyrazole were purchased from TCI America. Formaldehyde, acetaldehyde, styrene oxide, N-succinimide, THF, and methanol were purchased from Sigma-Aldrich (St. Louis, Mo.).

Synthesis of (1H-pyrazol-1-yl)methanol

A roundbottom flask comprising pyrazole (144 mmol, 100 g) and methanol (about 200 mL) was charged with formaldehyde (131 g, 37% aq. solution). The reaction mixture was stirred at 25° C. for 4 hours to give a homogenous solution. The solvent was removed under reduced pressure and dried in vacuo for 24 hours, yielding the title compound (127 g, 90%).

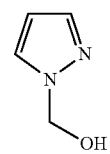

Synthesis of 1-(3,5-dimethyl-1H-pyrazol-1-yl)ethan-1-ol

A roundbottom flask comprising 3,5-dimethylpyrazole (10.4 mmol, 1.00 g) and THF (10 mL) was charged with acetaldehyde (10.4 mmol, 0.58 ml). The reaction mixture was stirred at 25° C. for 6 hours. The solvent was removed under reduced pressure and the solid was dried in vacuo, yielding the title compound (1.24 g, 85% yield).

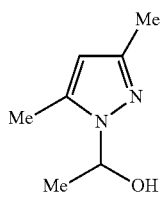

Synthesis of (3,5-dimethyl-1H-pyrazol-1-yl)(phenyl)methanol

A roundbottom flask comprising 3,5-dimethylpyrazole (10.4 mmol, 1.00 g) and xylene (10 mL) was charged with styrene oxide (10.4 mmol, 1.19 ml). The reaction mixture was stirred and refluxed at 140° C. for 6 hours. The reaction mixture was cooled to room temperature. The solid was collected by filtration, washed with xylene, and dried at 50° C., yielding the title compound (1.68 g, 80% yield).

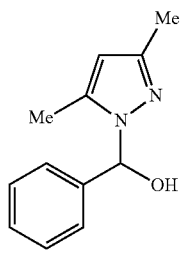 [SMILES: Cc1cc(C)n(C(O)c2ccccc2)n1]

Synthesis of 4-chloro-3,5-dimethyl-1H-pyrazole. A roundbottom flask comprising 3,5-dimethylpyrazole (10.4 mmol, 1.00 g) and N-succinimide (10.4 mmol, 1.39 g) was charged with chloroform (10 mL). The reaction mixture was stirred at 25° C. for 2 hours. The mixture was partitioned between chloroform and water. The organic phase was washed with water and brine and dried over $Na_2SO_4$. The mixture was filtered and solvent was removed in vacuo, yielding the title compound (1.15 g, 85% yield).

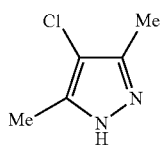

EXAMPLE 2

This Example illustrates the corrosion rate of copper in accordance with an embodiment of the present invention.

The corrosion rate of copper in the presence of (1H-pyrazol-1-yl)methanol, (3,5-dimethyl-1H-pyrazol-1-yl)methanol, (3,5-dimethyl-1H-pyrazol-1-yl)(phenyl)methanol, 1-(3,5-dimethyl-1H-pyrazol-1-yl)ethan-1-ol, 2-(1H-pyrazol-1-yl)ethan-1-ol, 3-phenyl-1H-pyrazole, 4-chloro-3,5-dimethyl-1H-pyrazole, and 3,5-dimethylpyrazole was determined using linear polarization resistance measurements. In addition, the corrosion rate of copper in the presence of pyrazole, 1-ethyl-1H-pyrazole, and tolyltriazole was determined using linear polarization resistance measurements. (1H-Pyrazol-1-yl)methanol, (3,5-dimethyl-1H-pyrazol-1-yl)methanol, (3,5-dimethyl-1H-pyrazol-1-yl)(phenyl)methanol, 4-chloro-3,5-dimethyl-1H-pyrazole, and 1-(3,5-dimethyl-1H-pyrazol-1-yl)ethan-1-ol were prepared by Applicants. Pyrazole, 3,5-dimethylpyrazole, 2-(1H-pyrazol-1-yl)ethan-1-ol, and 1-ethyl-1H-pyrazole were purchased from TCI America. 3-Phenyl-1H-pyrazole and tolyltriazole were purchased from Sigma-Aldrich (St. Louis, Mo.).

For each experiment, cylindrical copper coupons pre-polished using SIC 600 paper and fitted on a Pine rotator were immersed in a solution of corrosion inhibitor. The test solution comprised 470 ppm calcium, 230 ppm magnesium, 590 ppm chloride, 260 ppm sulfate, and 100 ppm alkalinity, as $CaCO_3$. The pH of the test water was maintained at 7.0 using carbon dioxide, and the water temperature was maintained at 45° C. throughout the experiment.

The copper samples were immersed in 1 liter electrochemical cells comprising a 5 ppm inhibitor solution, and the Rp (polarization resistance) was recorded over a 24 hour period. The analysis was conducted using the following testing conditions: Initial E: −0.02V; Final E: +0.02V; Scan rate: 0.5 mV/s; Sample period: 1 second; Repeat time: 15 minutes; Sample area: 5 $cm^2$; Density: 8.92 $g/cm^3$; Copper Eq. Weight: 63.54 g; and Initial delay: 30 seconds.

Figure 2:
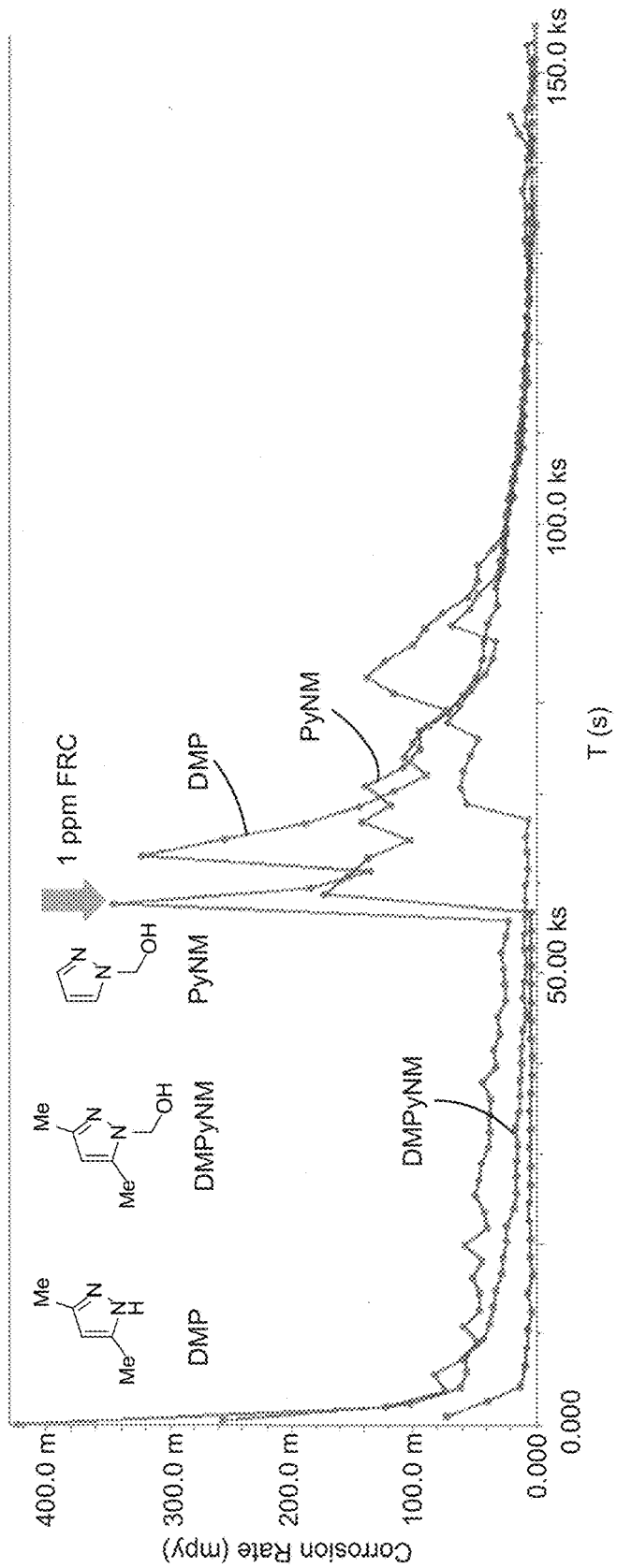
FIG. 2 is a line graph that illustrates the corrosion rate of copper using (1H-pyrazol-1-yl)methanol, 3,5-dimethylpyrazole, or (3,5-dimethyl-1H-pyrazol-1-yl)methanol as a corrosion inhibitor in the absence and presence of bleach.
Figure 3:
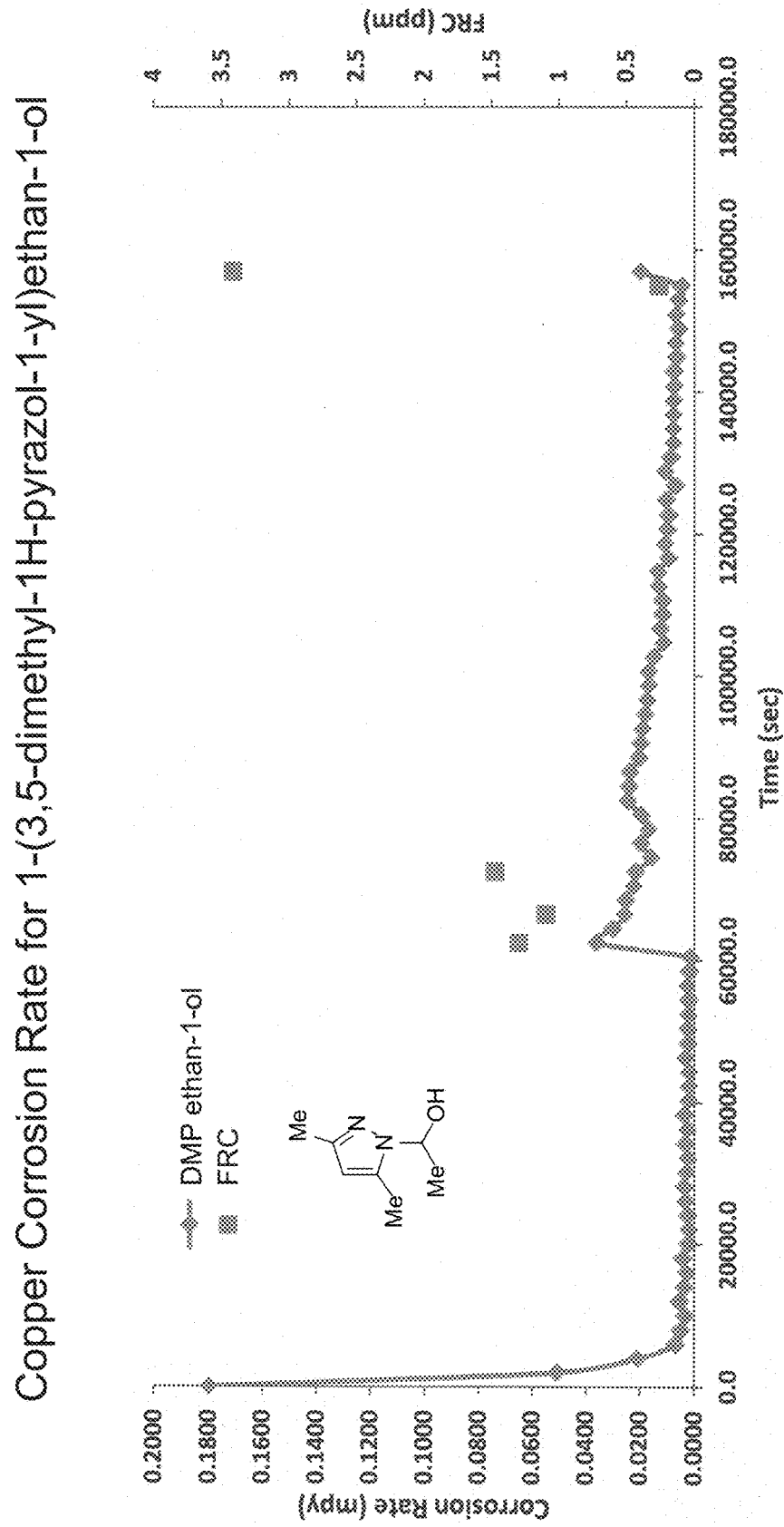
FIG. 3 is a line graph that illustrates the corrosion rate of copper using 1-(3,5-dimethyl-1H-pyrazol-1-yl)ethan-1-ol as a corrosion inhibitor in the absence and presence of bleach.

Next, the copper samples were exposed to 1 ppm FRC by adding a few drops of 4% bleach solution to the electrolyte solution. After the FRC reached 1 ppm, the copper samples were analyzed. Throughout the analysis, the bleach solution was added intermittently to maintain the FRC at 1 ppm. The Rp in the absence and presence of bleach was collected and analyzed, and the average corrosion rate was calculated and recorded in Table 1. Corrosion rates were calculated in mils per year (mpy). FIGS. 1-3 display data plots for compounds 1, 3, 5, 6, and 9.

As shown in Table 1 and FIGS. 1-3, compounds 1-6 provide copper corrosion rates less than 0.1 mpy. In particular, compounds 1-3 greatly decrease the rate of copper corrosion. The data suggests that alcohol substitution at the 1-position of the pyrazole provides an overall decrease in the rate of copper corrosion. For example, it was surprisingly and unexpectedly discovered that (1H-pyrazol-1-yl)methanol (compound 1) provides greater corrosion protection than pyrazole (compound 9). In addition, (3,5-dimethyl-1H-pyrazol-1-yl) methanol (compound 5) provides a lower corrosion rate than 3,5-dimethylpyrazole (compound 6). Moreover, the data suggests that substitution with secondary alcohols can provide enhanced corrosion inhibition (e.g., compounds 2 and 3 vs. compound 5).

Upon the addition of bleach, it was found that compounds of the present method provide good protection against copper corrosion. The corrosion rate of copper in the presence of compounds 1-3, 5, and 6 remained well below 0.1 mpy in the presence of bleach, and provide greater corrosion protection than pyrazole and tolyltriazole.

This Example illustrates that a method of an embodiment of the present invention can reduce the rate of copper corrosion. Moreover, this Example illustrates that a method of an embodiment of the present invention can provide greater corrosion resistance in the presence of an oxidizing halogen than commonly used corrosion inhibitors such as tolyltriazole.

TABLE 1

| Compound No. | Compound Name | No FRC Corrosion Rate (mpy) | 1 ppm FRC Corrosion Rate (mpy) |
|---|---|---|---|
| 1 | (1H-pyrazol-1-yl)methanol (PyNM) | 0.0057 | 0.0296 |
| 2 | (3,5-dimethyl-1H-pyrazol-1-yl)(phenyl)methanol | 0.0043 | 0.0479 |
| 3 | 1-(3,5-dimethyl-1H-pyrazol-1-yl)ethan-1-ol | 0.0036 | 0.0142 |
| 4 | 2-(1H-pyrazol-1-yl)ethan-1-ol | 0.0212 | 0.2739 |
| 5 | (3,5-dimethyl-1H-pyrazol-1-yl)-methanol (DMPyNM) | 0.0197 | 0.0228 |
| 6 | 3,5-dimethylpyrazole (DMP) | 0.0396 | 0.0599 |
| 7 | 4-chloro-3,5-dimethyl-1H-pyrazole (ClDMP) | 0.0025 | 0.0212 |
| 8 | 3-phenyl-1H-pyrazole (PhPy) | 0.0039 | 0.0916 |
| 9 | Pyrazole (Py) | 0.4232 | 0.1666 |
| 10 | 1-ethyl-1H-pyrazole | 0.0345 | 0.5932 |
| 11 | Tolyltriazole (TT) | 0.0214 | 0.0995 |

EXAMPLE 3

This Example illustrates the solubility of compounds of formulae (I) and (II) at various pH levels in accordance with an embodiment of the invention.

Solutions comprising (1H-pyrazol-1-yl)methanol and 3,5-dimethylpyrazole at various pH levels were prepared by dissolving the corresponding pyrazole (2 grams) in deionized water (98 grams). The solutions were adjusted to the desired pH by adding dilute sulfuric acid or aqueous sodium hydroxide (1 N). The turbidity of each solution was measured using a HACH 2100Q Portable Turbidimeter.

Figure 4:
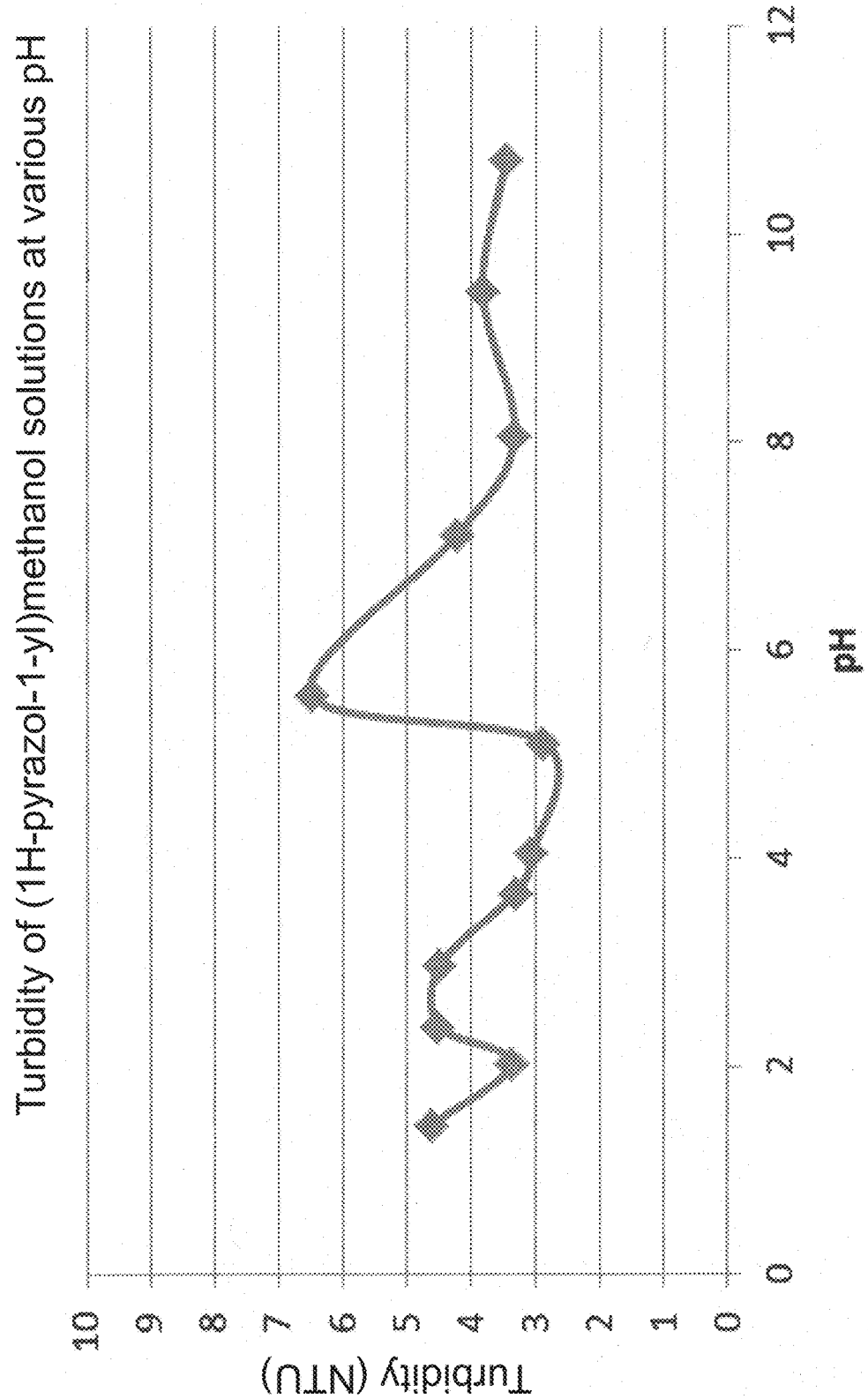
FIG. 4 is a line graph that illustrates the turbidity of a solution comprising (1H-pyrazol-1-yl)methanol at various pH levels.
Figure 5:
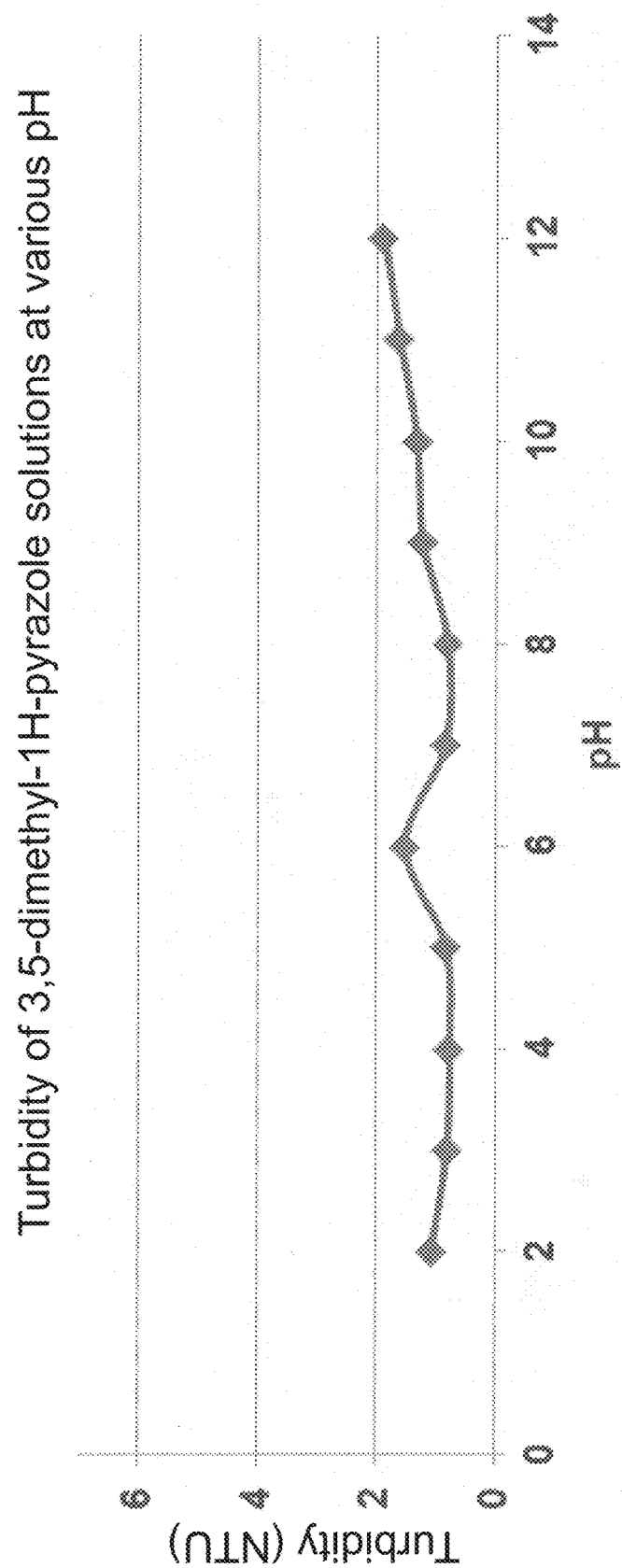
FIG. 5 is a line graph that illustrates the turbidity of a solution comprising 3,5-dimethylpyrazole at various pH levels.

As shown in FIGS. 4 and 5, the measured turbidity for all analyzed solutions was less than 7 NTU, confirming that (1H-pyrazol-1-yl)methanol and 3,5-dimethylpyrazole are water soluble and can be formulated at a wide-range of pH levels.

EXAMPLE 4

This Example illustrates the aquatic toxicity of a corrosion inhibitor in accordance with an embodiment of the present invention.

The aquatic toxicity of (1H-pyrazol-1-yl)methanol toward a variety of species was analyzed. The toxicity data is listed in Table 2. (1H-pyrazol-1-yl)methanol had lower aquatic toxicity than many commonly used corrosion inhibitors. For example, (1H-pyrazol-1-yl)methanol had a $LC_{50}$ of >100 in the presence of *Oncorhynchus mykiss*.

TABLE 2

Aquatic Toxicity Data for (1H-pyrazol-1-yl)methanol

| Test Name | NOEC (survival) | $LC_{50}$ (mg/L) | $IC_{50}$ (mg/L) |
|---|---|---|---|
| Chronic 72-Hour Green Algal Growth Test using *Pseudokirchneriella subcapita* | 2.5 mg/L | — | 3.829 |
| *Ceriodaphnia dubia* 48-Hour Definitive Toxicity Test | 13 mg/L | 31.5 (28.1-35.3) | — |
| *Oncorhynchus mykiss* 96-Hour Definitive Toxicity Test | 50 mg/L | >100 | — |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for inhibiting corrosion of a metal surface in contact with an aqueous system, the method comprising adding to the aqueous system a compound of formula (I),

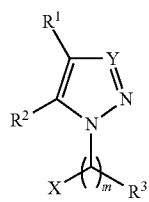

formula (I)

wherein X is selected from the group consisting of —OH, —NH₂, —SH, and halogen;

Y is selected from the group consisting of —CR⁴ and nitrogen;

R¹ and R² form a six-membered aromatic ring or each of R¹ and R² is the same or different and selected from the group consisting of hydrogen, aryl, heteroaryl, C₁-C₁₆ alkyl, C₂-C₁₆ alkenyl, C₂-C₁₆ alkynyl, C₃-C₈ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl;

R³ is selected from the group consisting of hydrogen, aryl, heteroaryl, C₁-C₁₆ alkyl, C₂-C₁₆ alkenyl, C₂-C₁₆ alkynyl, C₃-C₈ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl;

R⁴ is selected from the group consisting of hydrogen, aryl, heteroaryl, C₁-C₁₆ alkyl, C₂-C₁₆ alkenyl, C₂-C₁₆ alkynyl, C₃-C₈ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl;

m is an integer of from 1 to 9; or a salt thereof;

with the proviso that when m=2, R¹=H, and Y=CR⁴ wherein R⁴ is methyl, then R² is not methyl or pyridinyl;

and the aqueous system comprises an oxidizing halogen compound and pH of from about 6 to about 12, wherein the oxidizing halogen compound is selected from chlorine bleach, chlorine, bromine, iodine, hypochlorite, hypobromite, iodine/hypoiodous acid, hypobromous acid, halogenated hydantoins, chlorine dioxide, a stabilized version of hypochlorous or hypobromous acid, and any combination thereof.

2. The method of claim 1, wherein the compound of formula (I) is

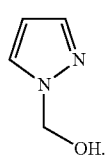

3. The method of claim 1, wherein the compound of formula (I) is

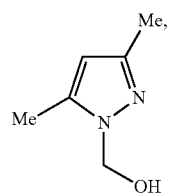

wherein Me is methyl.

4. The method of claim 1, wherein the compound of formula (I) is

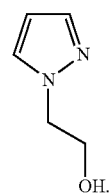

5. The method of claim 1, wherein the compound of formula (I) is

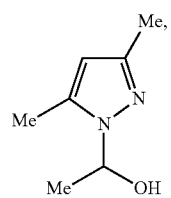

wherein Me is methyl.

6. The method of claim 1, wherein the compound of formula (I) is

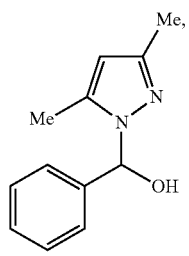

wherein Me is methyl.

7. The method of claim 1, wherein the metal surface comprises copper or a copper alloy.

8. The method of claim 1, wherein the aqueous system is a cooling water system.

9. The method of claim 1, wherein the metal has a corrosion rate of about 0.1 mpy or less.

10. The method of claim 1, wherein the compound of formula (I) has a LC₅₀ of greater than 100 mg/L.

11. A method for inhibiting corrosion of a metal surface in contact with an aqueous system, the method comprising adding to the aqueous system a compound of formula (II), formula (II)

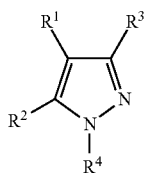

wherein each of $R^1$, $R^2$, and $R^3$ is the same or different and selected from the group consisting of hydrogen, aryl, heteroaryl, $C_1$-$C_{16}$ alkyl, $C_2$-$C_{16}$ alkenyl, $C_2$-$C_{16}$ alkynyl, $C_3$-$C_8$ cycloalkyl, benzyl, alkylheteroaryl, halogen, halosubstituted alkyl, amino, aminoalkyl, cyano, hydroxyl, alkoxy, thiol, alkylthio, carbonyl, nitro, phosphoryl, phosphonyl, and sulfonyl;

$R^4$ is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl; or a salt thereof;

with the proviso that when $R^1$ and $R^4$ are H, and $R^2$ is methyl, then $R^3$ is not alkylpyrazolyl or pyridinyl; and the aqueous system comprises an oxidizing halogen compound and has a pH of from about 6 to about 12, wherein the oxidizing halogen compound is selected from chlorine bleach, chlorine, bromine, iodine, hypochlorite, hypobromite, iodine/hypoiodous acid, hypobromous acid, halogenated hydantoins, chlorine dioxide, a stabilized version of hypochlorous or hypobromous acid, and any combination thereof.

12. The method of claim 11, wherein the compound of formula (II) is

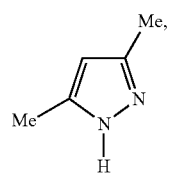

wherein Me is methyl.

13. The method of claim 11, wherein the compound of formula (II) is

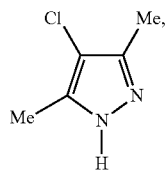

wherein Me is methyl.

14. The method of claim 11, wherein the metal surface comprises copper or a copper alloy.

15. The method of claim 11, wherein the metal has a corrosion rate of about 0.1 mpy or less.

* * * * *

UNITED STATES PATENT AND TRADEMARK OFFICE
CERTIFICATE OF CORRECTION

PATENT NO.         : 10,519,116 B2
APPLICATION NO.    : 15/166536
DATED              : December 31, 2019
INVENTOR(S)        : Harbindu et al.

Page 1 of 1

It is certified that error appears in the above-identified patent and that said Letters Patent is hereby corrected as shown below:

At Column 23, Claim 1, Line 41, delete "$R^1\!\!=\!\!H$, and Y=$CR^4$" and insert --$R^1 = H$, and Y=$CR^4$--

Signed and Sealed this
First Day of December, 2020

Andrei Iancu
*Director of the United States Patent and Trademark Office*